United States Patent [19]

Barber, Jr. et al.

[11] Patent Number: 5,190,547
[45] Date of Patent: Mar. 2, 1993

[54] REPLICATOR FOR RESECTING BONE TO MATCH A PATTERN

[75] Inventors: Forest C. Barber, Jr., Bedford; Durrell G. Tidwell, Crowley, both of Tex.

[73] Assignee: Midas Rex Pneumatic Tools, Inc., Ft. Worth, Tex.

[21] Appl. No.: 883,685

[22] Filed: May 15, 1992

[51] Int. Cl.⁵ .................... A61B 17/00; A61F 5/00
[52] U.S. Cl. ............................. 606/79; 606/86
[58] Field of Search .............. 606/86, 87, 88, 79; 128/888; 409/80, 84

[56] References Cited

U.S. PATENT DOCUMENTS

| | | | |
|---|---|---|---|
| 4,643,622 | 2/1987 | Winski | 409/84 |
| 4,730,616 | 3/1988 | Frisbie | 606/87 |
| 5,007,912 | 4/1991 | Albrektsson | 606/87 |
| 5,057,112 | 10/1991 | Sherman | 606/86 |
| 5,086,401 | 2/1992 | Glassman | 606/88 |
| 5,112,336 | 5/1992 | Krevolin | 606/87 |

*Primary Examiner*—Michael A. Brown
*Attorney, Agent, or Firm*—James E. Bradley

[57] ABSTRACT

A device for resecting a bone utilizes a pattern to control the cutting tip for the resection. The device has a frame with a pattern holder and a bone holder. A tool holder mounts to the frame by means of a four bar linkage assembly. The tool holder has a cutting tool and a probe mounted to it. The four bar linkage allows three-dimensional movement of the tool holder, but constrains the tool holder to always be in parallel with a line extending through the pattern holder and bone holder.

16 Claims, 5 Drawing Sheets

REPLICATOR FOR RESECTING BONE TO MATCH A PATTERN

BACKGROUND OF THE INVENTION

1. Field of the invention

This invention relates in general to equipment for resecting bones during implant and prosthetic surgery so as to match a pattern.

2. Description of the Prior Art

During certain types of orthopedic surgery, there is a need to cut or resect away part of the bone to a desired shape. For example, in the case of grafting a donor bone section to replace a diseased bone section, portions of the donor bone joint must be shaped to resemble the diseased bone joint as much as possible.

As another example, a tibial plateau prosthesis may be implanted in the leg of a user while retaining an existing femur. In that case, the existing femur must be resected to match the tibial plateau of the prosthesis as much as possible.

In the prior art, this is handled using high speed bone cutting or resecting equipment. A surgeon primarily relies on a visual comparison and skillful use of the equipment. The surgeon may also make molds to assist in performing the resection.

SUMMARY OF THE INVENTION

In this invention, a replicator apparatus for resecting the bone into a desired shape is provided that will precisely shape the bone to the pattern. The replicator includes a frame with a pattern holder and a bone holder. The pattern holder and the bone holder are spaced apart from each other on an X-axis, or bone-pattern axis. A tool holder holds a probe and a power cutting tool. The tips of the probe and the cutting tool are mounted on a line that is parallel to the tool holder axis.

A linkage means connects the tool holder with structure mounted to the frame. The linkage means comprises two pairs of parallel bars, each forming parallelograms. These bars are pivotally mounted so as to allow free movement in three dimensions of the tool holder. However, the bars will always maintain the tool holder parallel to the bone-pattern axis. The user traces the tip of the probe over the pattern while operating the cutting tool to shape the bone to match the pattern.

DETAILED DESCRIPTION OF THE INVENTION

Figure 1:
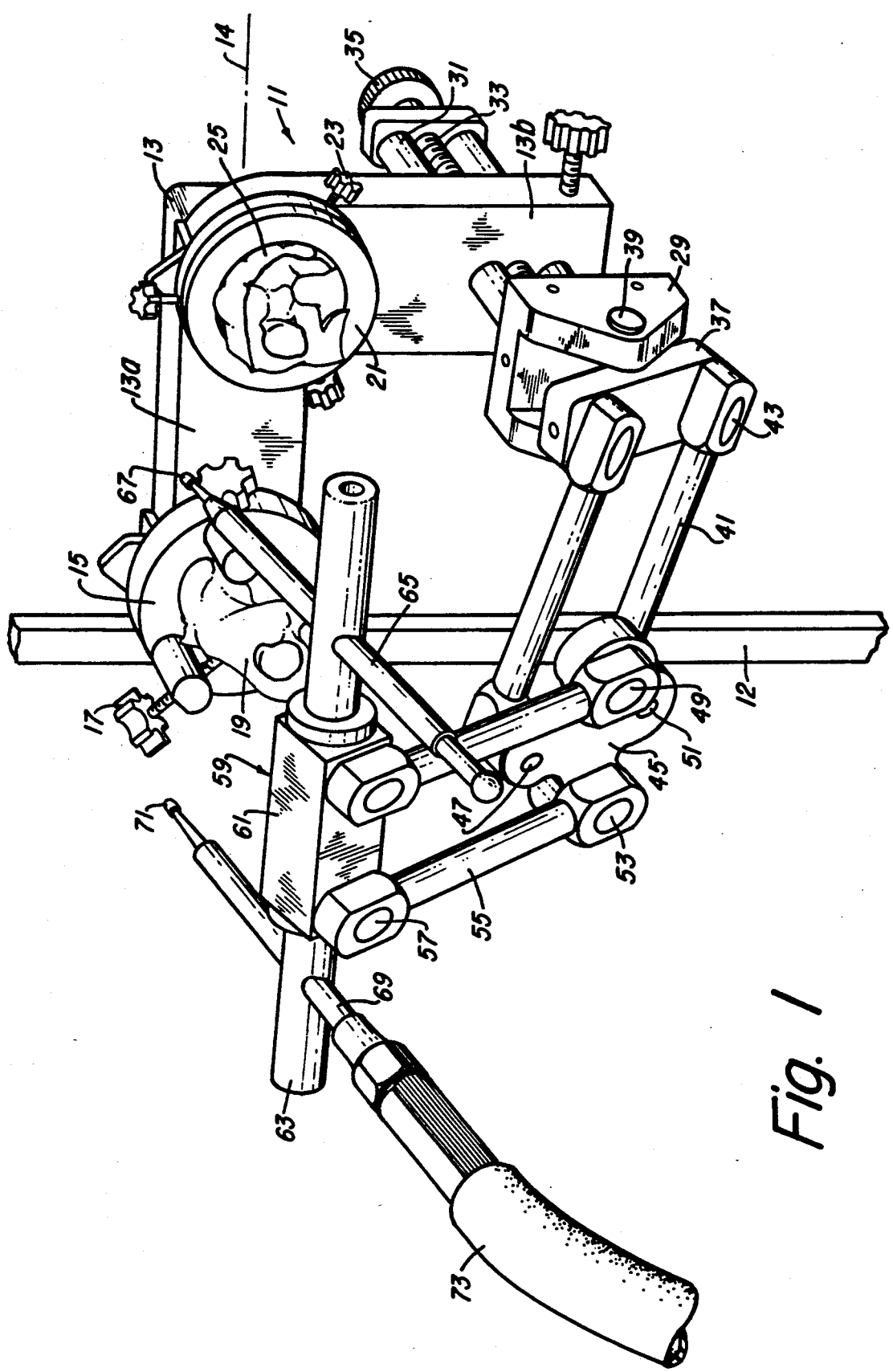
FIG. 1 is a perspective view showing a first embodiment of a replicator apparatus constructed in accordance with this invention.
Figure 2:
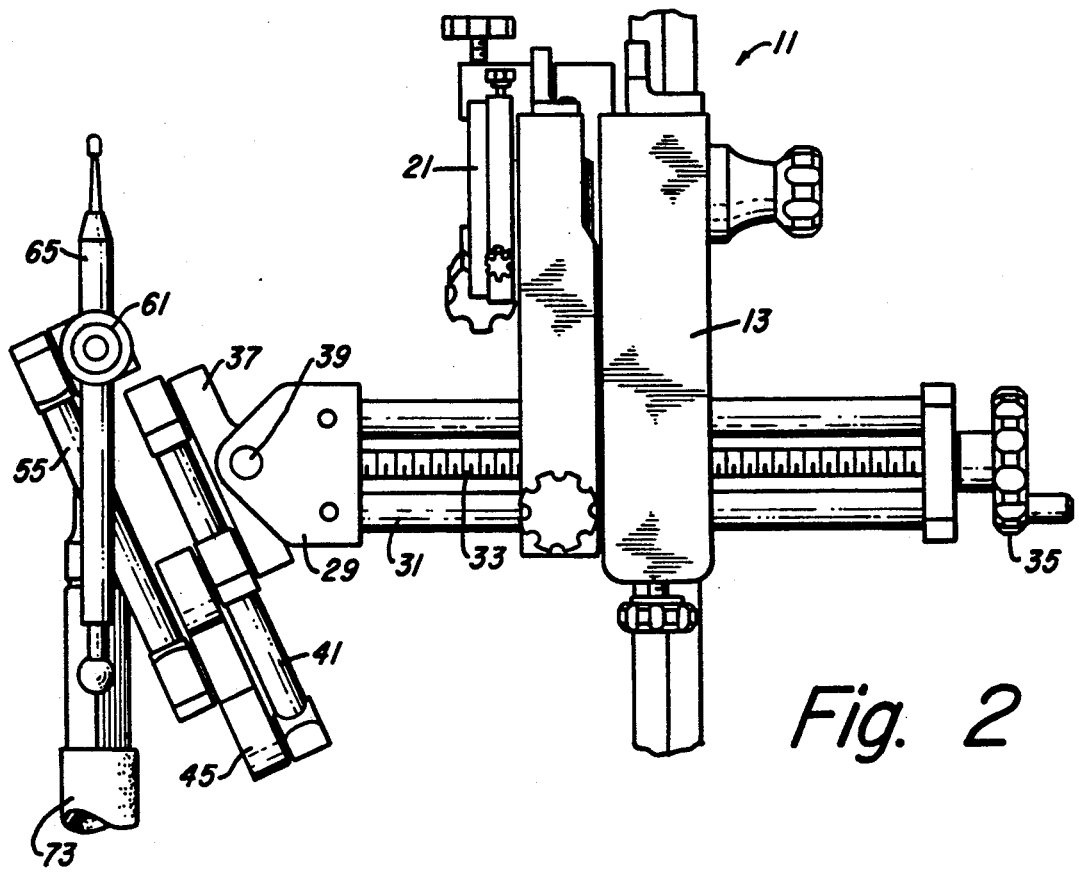
FIG. 2 is a side view of the replicator of FIG. 1.
Figure 3:
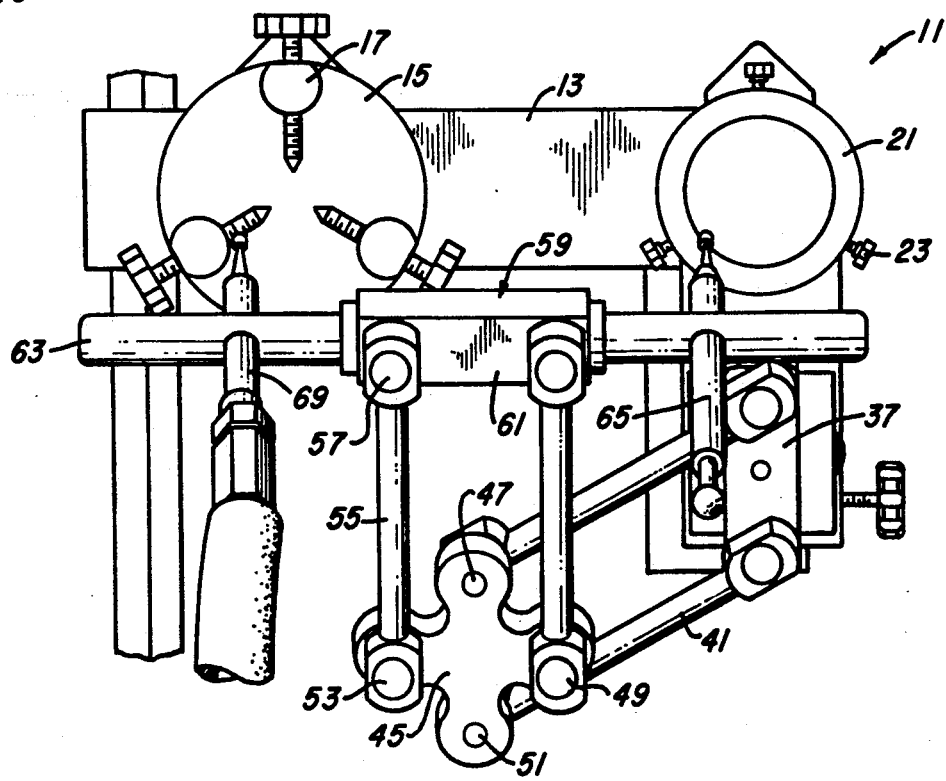
FIG. 3 is a front view of a portion of the replicator of FIG. 1.

Referring to FIG. 1, replicator 11 is constructed to be utilized in an operating room during surgery. Resecting replicator 11 has an L-shaped frame 13 which mounts to a vertical rod 12. Frame 13 has a horizontal or X-axis portion 13a, extending along an X-axis 14 and a vertical or Y-axis portion 13b, extending along a Y-axis 16. A bone holder means 15 having an axis perpendicular to X-axis 14 is mounted to frame 13. Bone holder 15 is a circular rotatable plate that has three screw clamps 17. Screw clamps 17 are spaced 120 degrees apart from each other for tightening against a section of a bone 19. In the embodiment of FIGS. 1-3, bone 19 will be a section of a donor bone for implanting in a human body. For example, bone 19 may be a femur of a knee joint. Preferably, bone holder 15 can be rotated relative to frame 13 about the axis of bone holder 15.

A pattern holder 21 is spaced from bone holder 15 along the X-axis 14. Pattern holder 21 is also a plate, having three screw clamps 23 for clamping a pattern 25. The axis of pattern holder 21 will be perpendicular to and intersecting X-axis 14. In the embodiment of FIGS. 1-3, pattern 25 will be a mold formed by the surgeon during surgery.

A clevis 29 mounts to the lower end of the frame vertical portion 13b. Clevis 29 mounts to a pair of shafts 31, as illustrated also in FIG. 2. Clevis 29 is not rotatable relative to frame 13. A threaded rod 33 having a crank handle 35, will move clevis 29 forward and away from frame 13 Shafts 31 extend along a Z-axis which is perpendicular to X-axis 14 and also to Y-axis 16. A vertical line along the Y-axis 16 passing through shafts 31 would pass through the center of pattern 25.

Clevis 29 includes a rotatable clevis bracket 37. Clevis bracket 37 is secured by a pin 39 to spaced apart lobes of clevis 29. Pin 39 is mounted along a clevis axis that is parallel to X-axis 14 and perpendicular to shafts 31. Pin 39 allows clevis bracket 37 to swing in a Z-axis plane.

A pair of frame parallel bars 41 pivotally mount to clevis bracket 37. Frame parallel bars 41 are identical in length and size and mounted so as to always be parallel to each other. Frame parallel bars 41 each have a frame end mounted pivotally to clevis bracket 37 by spaced apart clevis bracket pivot pins 43. Pivot pins 43 are spaced apart from each other along the Y-axis 16. Pivot pins 43 allow rotation of frame parallel bars 41 in a plane containing frame parallel bars 41.

The opposite ends, or plate ends, of frame parallel bars 41 connect to a linkage plate 45. Plate 45 is free floating and has four pivotal pins, referred to herein as a zero degree pin 47, a 90 degree pin 49, a 180 degree pin 51, and 270 degree pin 53. The zero degree pin 47 and the 180 degree pin 51 Will always be located on a line parallel to a plane containing Y-axis 16. The 90 degree pin 49 and 270 degree pin 53 will always be located on a line parallel to X-axis 14. The frame parallel bars 41 connect to the zero degree pin 47 and 180 degree pin 51. In the embodiment shown, the ends of the frame parallel bars 41 are located on the side of plate 45 that faces frame 13.

A pair of tool holder parallel bars 55 have plate ends that connects to the 90 degree pin 49 and 270 degree pin 53. Tool holder parallel bars 55 are of identical length and are maintained always in parallel relationship to each other. The ends of tool holder parallel bars 55 are located on a side of plate 45 that faces away from frame 13.

The opposite ends of tool holder parallel bars 55 pivotally connect to tool holder pivot pins 57 of a tool holder 59. The distance between pivot pins 57 is the same as the distance between pivot pins 49 and 53. Similarly, this distance is the same as between pivot pins 47, 51 and the pivot pins 43. Tool holder 59 includes a tool holder sleeve 61 which supports pivot pins 57. An extension member 63 extends completely through tool holder sleeve 61. Extension member 63 extends on opposite sides of sleeve 61 and is rotatable relative to sleeve 61. A tool holder axis extends along extension member 63. The tool holder axis is maintained by the parallel bars 41, 55 in a parallel relationship to X-axis 14 at all times.

A stylus or probe 65 mounts to the right side of extension sleeve 61. Probe 65 is frictionally held in a hole extending through extension member 63. Probe 65 has a tip 67 that will trace over the contour of pattern 25. The tip 67 will be placed such that when touching the pattern 25, the clevis bracket 37 will be in a near vertical orientation.

Cutting tool 69 is secured in a hole provided in extension member 63 on the opposite side of sleeve 61. Cutting tool 69 is a conventional high speed pneumatic cutting instrument. Cutting tool 69 has a tip 71 that will contain a bit or other type of cutting tool for resecting the bone 19. Tip 71 is spaced apart from tip 67 the same distance as from the centerline of bone holder 15 to the centerline of pattern holder 21. Also, probe tip 67 will be positioned so that a line passing through tips 67, 71 will be parallel with the axis of tool holder 59 and also parallel with X-axis 14. An air hose 73 applies air pressure to cutting tool 69 to form the cutting action.

In the operation of the embodiments of FIGS. 1-3, the surgeon will make a mold to form a pattern 25. This may be done by first cutting the diseased bone from the patient, then pressing a moldable material against the cut area in the patient. The material will harden into pattern 25, which is then placed in pattern holder 21. The surgeon takes the donor bone 19 and places it in bone holder 15. The surgeon will align the tips 67, 71 parallel with the axis of tool holder 59 by using a T-shaped template (not shown). The surgeon will rotate the crank handle 35 (FIG. 2) to extend clevis 29 to a desired orientation. In that orientation, probe tip 67 will be touching pattern 25, cutting tool 69 will be touching bone 19, and clevis bracket 37 will be oriented approximately parallel to Y-axis 16.

The surgeon will turn on cutting tool 69 to begin resecting bone 19. The surgeon will trace probe tip 67 over all portions of the contour of pattern 25. The parallel bars 41, 55 will allow the tool holder 59 to rotate freely in a plane parallel to the planes containing the parallel bars 41, 55. The clevis bracket 37 will allow the tool holder 59 to rotate about clevis bracket pin 39 in Z-axis directions. This provides three-dimensional movement. The parallel bars 41, 55, however, construct the tool holder 59 such that the tool holder 59 will always be parallel to the X-axis 14. This assures that the section on the bone 19 will precisely match the pattern 25. Once completed, the surgeon will remove donor bone 19 and implant it in the patient.

Figure 4:
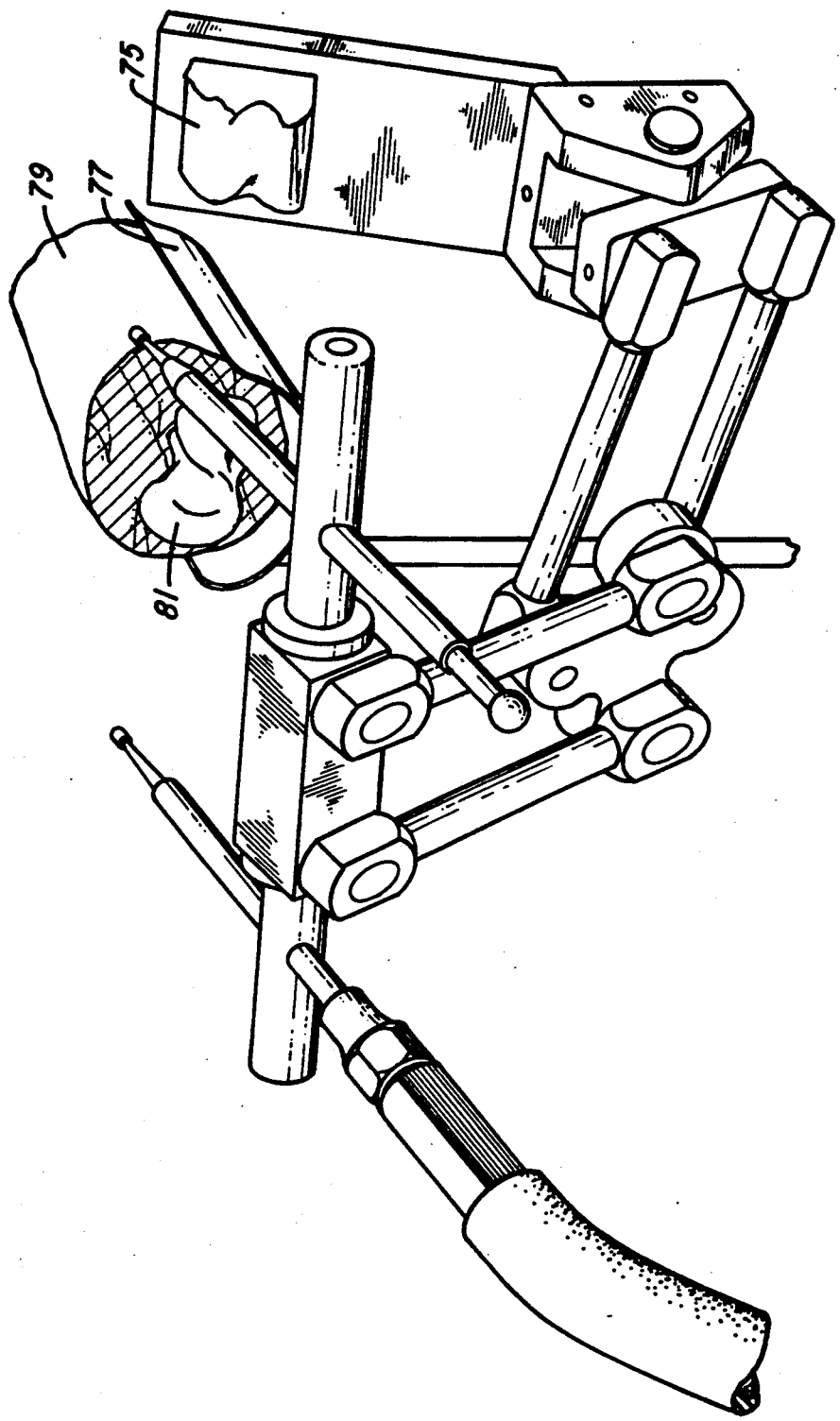
FIG. 4 is a perspective view illustrating a second embodiment of a replicator apparatus constructed in accordance with this invention.

FIG. 4 illustrates an alternate embodiment. The resecting replicator is the same in most of its components, therefore these will not be discussed. It differs in that the pattern 75 will be a pattern based on a prosthesis to be installed in the patient. In this case, thigh support 77 will support the thigh 79 of the patient. The patient's femur 81 will be exposed. The surgeon will resect the patient's femur 81 so as to match pattern 75, which matches a tibial plateau to be installed. The tibial plateau is a prostheses.

Figure 5:
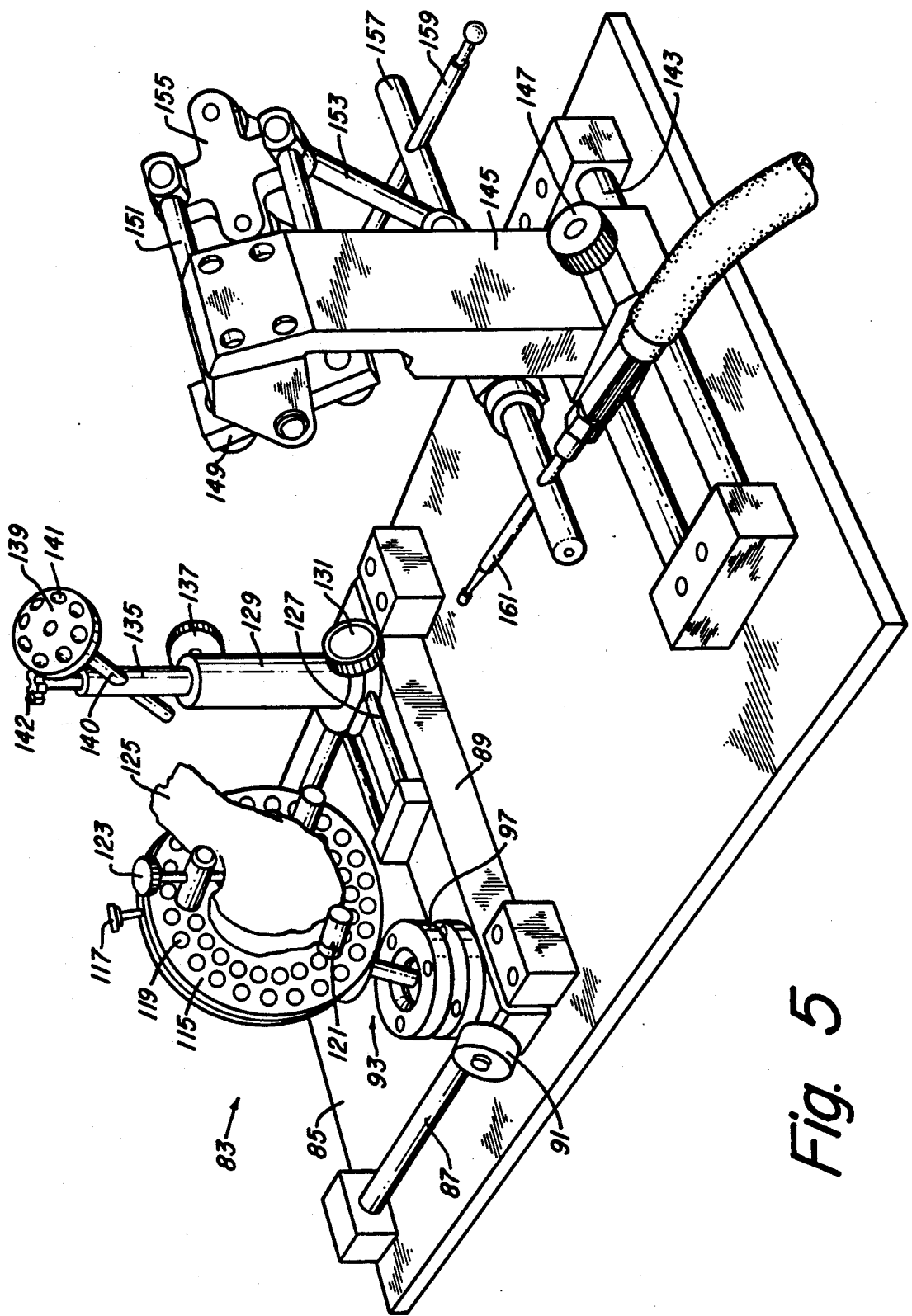
FIG. 5 is a perspective view of a third embodiment of a replicator apparatus constructed in accordance with this invention.
Figure 6:
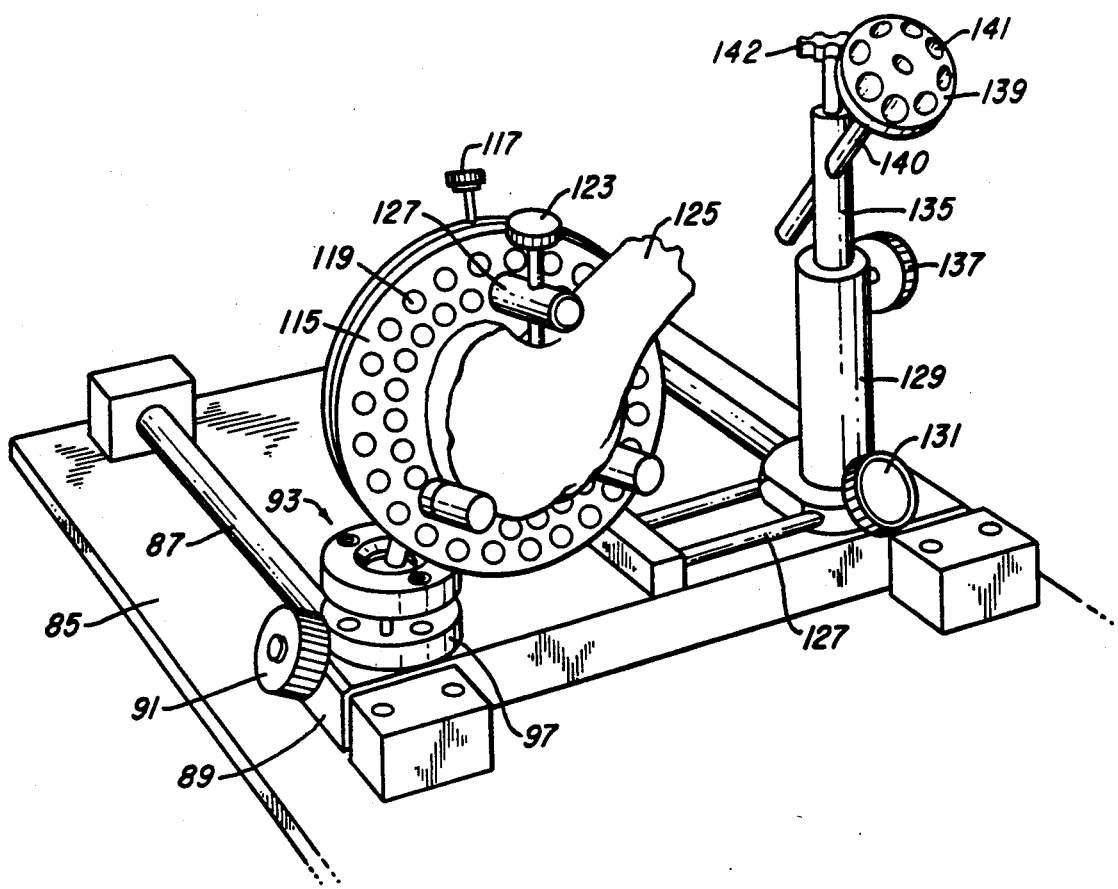
FIG. 6 is a perspective view of the bone holder and pattern holder of the replicator of FIG. 5.
Figure 7:
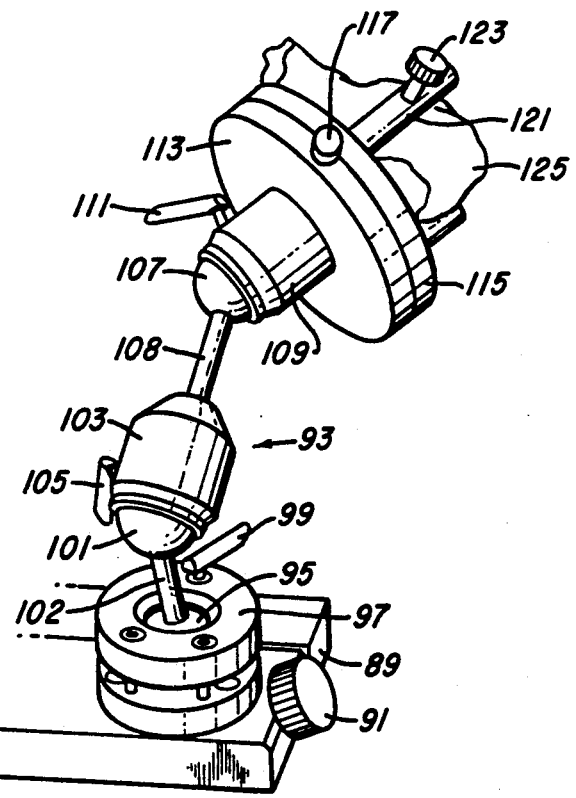
FIG. 7 is a perspective view of the bone holder of the replicator of FIG. 5.

FIGS. 5-7 show a third embodiment, which performs the same functions as replicator 11 of FIGS. 1-3, but has more adjustability. Replicator 83 has a frame that includes a base plate 85. Base plate 85 will rest on a table in the operating room. A pair of slides 87, which are smooth, cylindrical bars, are mounted to base plate 85. Slides 87 are oriented along a Z-axis. A platform 89 mounts slidably to slides 87. An adjusting screw 91 will secure platform 89 in a desired position relative to base plate 85.

A bone holder post 93 mounts to platform 89. Bone holder post 93 is adjustable in three dimensions, as illustrated in FIG. 7. Bone holder post 93 includes a lower ball 95 and socket 97. Ball 95 can move rotatably in socket 97 to allow orientation in three dimensions. Adjusting screw 99 will secure ball 95 in a desired position. An intermediate ball 101 connects to ball 95 by a stem 102. Ball 101 locates in a socket 103. It too can be adjusted in three dimensions by means of an adjusting screw 105. An upper ball 107 connects to socket 103 by a stem 108. Ball 107 locates in a socket 109. An adjusting screw 111 will secure socket 109 in a desired position relative to ball 107.

A stationary plate 113 mounts to socket 109. A rotatable plate 115 mounts rotatably to stationary plate 113. An adjusting screw 117 will lock rotating plate 115 in a desired position. Referring to FIG. 5, the forward face of rotating plate 115 has a large number of screw holes 119. Three or more studs 121 can be secured to any of the screw holes 119. At least one of the studs 121 supports a screw clamp 123 which engages a donor bone 125. Screw clamp 123 and two of the other studs 121 will secure the donor bone 125 in a desired orientation.

A pair of slides 127 are mounted on platform 89 perpendicular to slides 87. A pattern post 129 mounts slidably to slides 127. An adjusting screw 131 allows pattern post 129 to be positioned at desired points along slides 127. Pattern post 129 is of a telescoping type, having an upper section 135 which telescopes upward from a lower section. An adjusting screw 137 will adjust the overall height of pattern post 129.

A pattern holder 139 mounts to the upper section 135 of pattern post 129. Pattern holder 139 has a plurality of holes 141 on its face to enhance the adherence of a clay-like mold (not shown) placed thereon. Pattern holder 139 is a disk, slightly convex on its face. Pattern holder 139 is mounted to a stem 140 that extends slidingly through the pattern post upper section 135. An adjusting screw 142 will secure stem 140 in a desired position. Stem 140 intersects pattern post upper section 135 at about a 45 degree angle. Slides 127, upper pattern post section 135, and stem 140 allow adjustment of pattern holder 139 in three dimensions.

A pair of slides 143 are mounted to base plate 85 perpendicular to slides 87. A tool holder post 145 mounts to slides 143. An adjusting screw 147 will allow tool holder post 145 to slide and be tightened to a selected position along slides 143.

The remaining portions of replicator 83 are the same as in the embodiment of FIGS. 1-4, thus will not be discussed in as much detail. These remaining portions include a clevis bracket 149 that mounts pivotally to the upper end of tool holder post 145. A pair of frame parallel bars 151 pivotally mount to clevis bracket 149. A pair of tool holder parallel bars 153 pivotally connect to the frame parallel bars 151 by means of a linkage plate 155. A tool holder 157 mounts pivotally to tool holder parallel bars 153. A probe 159 mounts to one side of tool holder 157. A cutting tool 161 mounts to the opposite side of tool holder 157.

Replicator 83 operates in the same manner as replicator 11 of FIGS. 1-3. A T-shaped template (not shown) will be employed to make sure that the tip of cutting tool 161 is aligned with the tip of probe 159 along an axis that is parallel to slides 143. The surgeon will adjust the various adjusting screws of the bone holder post 93 and pattern post 129 so that centerlines of bone holder plate 115 and pattern holder 139 will be the same distance apart as the distance between cutting tool 161 and probe 159. The centerlines of bone holder 115 and pattern holder 139 will be on a bone-pattern axis that is parallel with slides 143. The Z-direction distance, which is the distance parallel to slides 87, is adjusted by moving platform 89 along slides 87. The surgeon will trace probe 159 over the mold (not shown) while resecting the donor bone 125.

The invention has significant advantages. The four bar linkage allows a user to trace on a pattern to assure that the resecting will match that of the pattern. This reduces the amount of resection required It also will be easier to operate than relying on skill of a surgeon using visual comparisons.

While the invention has been shown in only two of its forms, it should be apparent to those skilled in the art that it is not so limited, but is susceptible to various changes without departing from the scope of the invention.

We claim:

1. An apparatus for resecting a bone into a desired shape, comprising in combination:
   a frame having an x-axis, a y-axis, and a z-axis;
   pattern holder means on the frame for holding a pattern representing the desired shape of the bone;
   bone holder means on the frame for holding the bone to be resected on the frame, the bone holder means being spaced apart from the pattern holder means along the x-axis;
   a tool holder having a tool holder axis;
   probe means mounted rigidly to the tool holder and having a tip for tracing over the contour of the pattern;
   cutting tool means mounted rigidly to the tool holder and having a tip for resecting the bone in a contour that is the same as the pattern while the probe means is traced over the pattern;
   the tips of the probe means and the cutting tool means being located on a line parallel to the tool holder axis;
   rotation means for rotating the probe means and the cutting tool means about the tool holder axis; and
   linkage means mounting the tool holder to the frame for allowing an operator to freely move the tool holder in three dimensions while maintaining the tool holder axis parallel to the x-axis.

2. The apparatus according to claim wherein the linkage means comprises:
   a four bar linkage assembly having two pairs of parallel bars mounted between the frame and the tool holder.

3. The apparatus according to claim wherein the linkage means comprises:
   a plate;
   a first pair of parallel bars, each having one end pivotally mounted to the tool holder and another end pivotally mounted to the plate; and
   a second pair of parallel bars, each having one end pivotally carried by the frame and another end pivotally mounted to the plate so as to position the first and second pairs of parallel bars in parallel planes.

4. The apparatus according to claim wherein the linkage means comprises:
   a plate having four pivot pins equally spaced in a circumferential array 90 degrees apart from each other;
   a first pair of parallel bars, each having a tool holder end and a plate end, the tool holder ends being pivotally mounted to the tool holder, the plate ends being pivotally mounted to two of the pivot pins of the plate which are spaced 180 degrees apart from each other; and
   a second pair of parallel bars, each having a frame end and a plate end, the frame ends being pivotally carried by the frame, the plate ends being pivotally mounted to two of the pivot pins of the plate which are spaced 180 degrees apart from each other, so as to position the first and second pairs of parallel bars in parallel planes.

5. The apparatus according to claim 1 wherein the linkage means comprises:
   a clevis carried by the frame, the clevis having a nonrotatable portion and a rotatable portion which rotates about a clevis axis which is parallel to the x-axis;
   a plate having four pivot pins equally spaced in a circumferential array 90 degrees apart from each other;
   a first pair of parallel bars, each having a tool holder end and a plate end, the tool holder ends being pivotally mounted to the tool holder, the plate ends being pivotally mounted to two of the pivot pins of the plate which are spaced 180 degrees apart from each other; and
   a second pair of parallel bars, each having a frame end and a plate end, the frame ends being pivotally carried by the rotatable portion of the clevis, the plate ends being pivotally mounted to two of the pivot pins of the plate which are spaced 180 degrees apart from each other, so as to position the first and second pairs of parallel bars in parallel planes, wherein the pivotally mounted ends of the first and second pairs of parallel bars allow rotation of the tool holder in planes parallel to the planes containing the parallel bars, and wherein the rotatable portion of the clevis allows movement of the tool holder in z-axis directions.

6. The apparatus according to claim 1 wherein the linkage means comprises:
   a clevis carried by the frame, the clevis having a support and a rotatable bracket which rotates relative to the support about a clevis axis which is parallel to the x-axis, the bracket having two spaced apart pivot pins which are spaced apart from each other along a line perpendicular to the clevis axis;
   a plate having a zero degree pivot pin, a 90 degree pivot pin, a 180 degree pivot pin, and a 270 degree pivot pin, the pivot pins being equally spaced in a circumferential array 90 degrees apart from each other;

a pair of tool holder parallel bars, each having a tool holder end and a plate end, the tool holder ends being pivotally mounted to the tool holder, the plate ends being pivotally mounted to the 90 degree and 270 pivot pins of the plate;

a pair of frame parallel bars, each having a frame end and a plate end, the frame ends being pivotally carried by the pivot pins of the bracket of the clevis, the plate ends being pivotally mounted to the zero degree and 180 degree pivot pins of the plate, wherein the pivotally mounted ends of the tool holder and frame parallel bars allow rotation of the tool holder in planes parallel to planes containing the parallel bars, and wherein the bracket of the clevis allows movement of the tool holder in z-axis directions; and wherein the apparatus further comprises means for moving the bone holder means and the support of the clevis apart and toward each other along a line that is parallel to the z-axis to selectively position the bone holder means relative to the tool holder means.

7. The apparatus according to claim wherein the frame comprises:
a base plate;
a bone holder post supported on and extending from the base plate for supporting the bone holder means;
a pattern holder post supported on and extending from the base plate for supporting the pattern holder means; and
a tool holder post supported on and extending from the base plate for supporting the linkage means and the tool holder means.

8. The apparatus according to claim wherein the frame comprises:
a base plate;
a bone holder post supported on and extending from the base plate for supporting the bone holder means;
adjusting means in the bone holder post for allowing selective positioning of the bone holder means in x, y, and z dimensions;
a pattern holder post supported on and extending from the base plate for supporting the pattern holder post;
adjusting means in the pattern holder post for allowing selective positioning of the pattern holder means in at least x and y directions; and
a tool holder post supported on and extending from the base plate for supporting the linkage means and the tool holder means.

9. An apparatus for resecting a bone into a desired shape, comprising in combination:
a frame;
pattern holder means carried on the frame for holding a pattern representing the desired shape of the bone;
bone holder means carried on the frame for holding the bone to be resected on the frame, the bone holder means being spaced apart from the pattern holder means a selected distance along an bone-pattern axis;
a tool holder having a tool holder axis, the tool holder having a sleeve member and an extension member mounted rotatably to the sleeve member, the extension member being located on a tool holder axis and being rotatable relative to the sleeve member on the tool holder axis;

a probe mounted rigidly to the tool holder extension member and having a tip for tracing over the contour of the pattern;

a cutting tool mounted rigidly to the tool holder extension member and having a tip for resecting the bone in a contour that is the same as the pattern while the probe is traced over the pattern, the cutting tool being spaced apart from the probe the same distance as between the pattern holder means and the bone holder means;

the tips of the probe means and the cutting tool means being located on a line parallel to the tool holder axis;

a pair of tool holder parallel bars carried in a plane, the tool holder parallel bars being pivotally mounted to the tool holder sleeve member so as to allow movement of the tool holder sleeve member in a plane parallel to the plane containing the first pair of parallel bars;

a pair of frame parallel bars carried in a plane;

means for carrying the frame parallel bars with the frame for allowing the second pair of parallel bars to rotate in the plane containing the second pair of parallel bars and also to rotate in a direction perpendicular to the plane containing the second pair of parallel bars; and means for connecting the two pairs of parallel bars together so as to maintain the two pairs of parallel bars in parallel planes and so as to allow the two pairs of parallel bars to rotate in said parallel planes.

10. The apparatus according to claim 9 wherein the means for carrying the second pair of parallel bars with the frame comprises:
a clevis carried by the frame, the clevis having a support and a rotatable bracket which rotates relative to the support about a clevis axis which is parallel to the bone-pattern axis, the bracket having two spaced apart pivot pins which are spaced apart from each other along a line perpendicular to the clevis axis, the frame parallel bars being pivotally mounted to the pivot pins; and
means for moving the bone support means and the support of the clevis toward and away from each other to selectively position the tool holder relative to the bone holder means.

11. The apparatus according to claim 10 wherein the means for connecting the two pairs of parallel bars together comprises:
a plate having four pivot pins equally spaced in a circumferential array 90 degrees apart from each other, each of the parallel bars being mounted to one of the pivot pins.

12. The apparatus according to claim 9 wherein the frame comprises:
a base plate;
a bone holder post supported on and extending from the base plate for supporting the bone holder means;
a pattern holder post supported on and extending from the base plate for supporting the pattern holder post; and a tool holder post supported on and extending from the base plate for supporting the linkage means and the tool holder means.

13. The apparatus according to claim 9 wherein the frame comprises:
a base plate;
a bone holder post supported on and extending from the base plate for supporting the bone holder means;
adjusting means in the bone holder post for allowing selective positioning of the bone holder means in at least two dimensions;
a pattern holder post supported on and extending from the base plate for supporting the pattern holder post;
adjusting means in the pattern holder post for allowing selective positioning of the pattern holder means in at least two directions; and
a tool holder post supported on and extending from the base plate for supporting the linkage means and the tool holder means.

14. An apparatus for resecting a bone into a desired shape, comprising in combination:
a frame;
pattern holder means carried on the frame for holding a pattern representing the desired shape of the bone;
bone holder means carried on the frame for holding the bone to be resected on the frame, the bone holder means being spaced apart from the pattern holder means a selected distance along a bone-pattern axis;
a tool holder having a tool holder axis, the tool holder having a sleeve member and an extension member mounted rotatably to the sleeve member, the extension member being located on a tool holder axis and being rotatable relative to the sleeve member on the tool holder axis;
a probe mounted rigidly to the tool holder extension member and having a tip for tracing over the contour of the pattern;
a cutting tool mounted rigidly to the tool holder extension member and having a tip for resecting the bone in a contour that is the same as the pattern as the probe is traced over the pattern, the cutting tool being spaced apart from the probe the same distance as between a centerline of the pattern holder means and a centerline of the bone holder means;
the tips of the probe means and the cutting tool means being located on a line parallel to the tool holder axis;
a clevis carried by the frame, the clevis having a nonrotatable support and a rotatable bracket which rotates relative to the support about a clevis axis which is parallel to the bone-pattern axis, the bracket having two spaced apart pivot pins which are spaced apart from each other along a line perpendicular to the clevis axis;
a plate having a zero degree pivot pin, a 90 degree pivot pin, a 180 degree pivot pin, and a 270 degree pivot pin, the pivot pins being equally spaced in a circumferential array 90 degrees apart from each other;
a pair of tool holder parallel bars, each having a tool holder end and a plate end, the tool holder ends being pivotally mounted to the tool holder sleeve member, the plate ends being pivotally mounted to the 90 degree and 270 pivot pins of the plate;
a pair of frame parallel bars, each having a frame end and a plate end, the frame ends being pivotally carried by the pivot pins of the bracket of the clevis, the plate ends being pivotally mounted to the zero degree and 180 degree pivot pins of the plate, wherein the pivotally mounted ends of the tool holder and frame parallel bars allow rotation of the tool holder in planes parallel to planes containing the parallel bars, and wherein the bracket of the clevis allows movement of the tool holder in directions perpendicular to the bone-pattern axis directions; and
extension means for moving the bone holder means and the clevis toward and apart from each other to selectively position the tool holder relative to the bone holder means.

15. The apparatus according to claim 14 wherein the frame comprises:
a base plate;
a bone holder post supported on and extending from the base plate for supporting the bone holder means;
adjusting means in the bone holder post for allowing selective positioning of the bone holder means in at least two dimensions;
a pattern holder post supported on and extending from the base plate for supporting the pattern holder post;
adjusting means in the pattern holder post for allowing selective positioning of the pattern holder means in at least two directions; and
a tool holder post supported on and extending from the base plate for supporting the linkage means and the tool holder means: and wherein the extension means comprises:
a pair of slides mounted on the base plate perpendicular to the bone-pattern axis;
a platform carried on the slides for selective movement relative to the base plate; and
means for mounting at least one of the posts on the platform to allow selective positioning of said post.

16. A method for resecting a bone into a desired shape, comprising in combination:
mounting a pattern holder and a bone holder to a frame, each of the pattern holder and bone holder having centerlines a selected distance apart from each other along an bone-pattern axis;
securing a pattern to the pattern holder representing the desired shape of the bone;
securing the bone in the bone holder;
mounting a probe and a power driven cutting tool in a tool holder, positioning the tip of the probe and the tip of the cutting tool the same distance apart from each other as the centerlines of the pattern holder and bone holder, and positioning the tips on a line that is parallel to the bone-pattern axis;
mounting the tool holder to the frame with a linkage assembly which allows an operator to freely move the tool holder in three dimensions while maintaining the tips of the probe and the cutting tool parallel to the bone-pattern axis; then
operating the cutting tool while tracing the contour of the pattern with the probe to resect the bone in a configuration matching the pattern.

* * * * *

UNITED STATES PATENT AND TRADEMARK OFFICE
CERTIFICATE OF CORRECTION

PATENT NO. : 5,190,547

DATED : March 2, 1993

INVENTOR(S) : Forest C. Barber, et al.

It is certified that error appears in the above-identified patent and that said Letters Patent is hereby corrected as shown below:

On the title page, item [75], should be corrected to read
-- Forest C. Barber, deceased, late of Bedford TX, by Forest
   C. Barber, Jr., executor; Durrell G. Tidwell, Crowley, TX.--

Signed and Sealed this

Seventh Day of December, 1993

*Attest:*

BRUCE LEHMAN

*Attesting Officer*  Commissioner of Patents and Trademarks